US009378723B2

(12) United States Patent
Bernal Castillo et al.

(10) Patent No.: US 9,378,723 B2
(45) Date of Patent: Jun. 28, 2016

(54) APPARATUS AND METHOD FOR ACQUIRING CONFIGURATION DATA

(71) Applicant: QUALCOMM Incorporated, San Diego, CA (US)

(72) Inventors: Ricardo De Jesus Bernal Castillo, San Diego, CA (US); Hyun Jin Park, San Diego, CA (US); Mark Adam Cherry, San Diego, CA (US); Wade Lyle Heimbigner, Vista, CA (US)

(73) Assignee: QUALCOMM Incorporated, San Diego, CA (US)

( * ) Notice: Subject to any disclaimer, the term of this patent is extended or adjusted under 35 U.S.C. 154(b) by 123 days.

(21) Appl. No.: 14/137,075

(22) Filed: Dec. 20, 2013

(65) Prior Publication Data

US 2015/0055789 A1 Feb. 26, 2015

Related U.S. Application Data

(60) Provisional application No. 61/868,966, filed on Aug. 22, 2013, provisional application No. 61/873,460, filed on Sep. 4, 2013.

(51) Int. Cl.
*A61F 11/06* (2006.01)
*G10K 11/178* (2006.01)

(52) U.S. Cl.
CPC ...... *G10K 11/178* (2013.01); *G10K 2210/1081* (2013.01); *G10K 2210/3028* (2013.01); *G10K 2210/3031* (2013.01); *G10K 2210/3033* (2013.01)

(58) Field of Classification Search
CPC .................. G10K 11/1788; G10K 2210/1081
USPC ........................................................ 381/71.1
See application file for complete search history.

(56) References Cited

U.S. PATENT DOCUMENTS

| | | | | |
|---|---|---|---|---|
| 7,305,254 | B2 | 12/2007 | Findikli | |
| 8,378,807 | B2 | 2/2013 | Lee et al. | |
| 8,443,096 | B2 | 5/2013 | Bolton et al. | |
| 2003/0118197 | A1* | 6/2003 | Nagayasu et al. | 381/74 |
| 2003/0229723 | A1 | 12/2003 | Kangas et al. | |
| 2008/0140868 | A1 | 6/2008 | Kalayjian et al. | |
| 2008/0159568 | A1* | 7/2008 | Asada et al. | 381/150 |
| 2008/0175402 | A1* | 7/2008 | Abe | G10K 11/178 381/71.6 |
| 2009/0179768 | A1* | 7/2009 | Sander | H04M 1/05 340/13.27 |

(Continued)

FOREIGN PATENT DOCUMENTS

| | | | |
|---|---|---|---|
| GB | 2497566 | A | 6/2013 |
| JP | 2009200902 | A | 9/2009 |

OTHER PUBLICATIONS

MAXIM-DS28EC20-20Kb1-Wire EEPROM, Rev 4, Mar. 2012, http://www.maximintegrated.com/datasheet/index. mvp/id/5453 viewed on Dec. 13, 2013, 27 pages.

(Continued)

*Primary Examiner* — Simon King
(74) *Attorney, Agent, or Firm* — Toler Law Group, PC

(57) ABSTRACT

A method includes detecting an accessory device at a master device. The method also includes receiving, at the master device, active noise cancellation (ANC) coefficients associated with the accessory device in response to detecting the accessory device. The method also includes modifying audio content, at the master device, based on the ANC coefficients.

30 Claims, 7 Drawing Sheets

(56) References Cited

U.S. PATENT DOCUMENTS

| | | | | |
|---|---|---|---|---|
| 2010/0167643 | A1* | 7/2010 | Hirsch | 455/41.1 |
| 2010/0233961 | A1 | 9/2010 | Holden et al. | |
| 2013/0108068 | A1* | 5/2013 | Poulsen et al. | 381/74 |
| 2013/0301846 | A1* | 11/2013 | Alderson et al. | 381/71.7 |

OTHER PUBLICATIONS

MAXIM Single-Channel 1-Wire Master with Sleep Mode, Rev 4, Jan. 2012, http://www.mouser.com/ds/2/256/DS2482-101-81852.pdf viewed on Dec. 13, 2013, 24 pages.

International Search Report and Written Opinion—PCT/US2014/053075—ISA/EPO—Feb. 5, 2015, 7 pages.

* cited by examiner

APPARATUS AND METHOD FOR ACQUIRING CONFIGURATION DATA

I. CLAIM OF PRIORITY

The present application claims priority from U.S. Provisional Patent Application No. 61/868,966, filed Aug. 22, 2013, entitled "ACCESSORY DEVICE WITH STORAGE CAPACITY," and U.S. Provisional Patent Application No. 61/873,460, filed Sep. 4, 2013, entitled "APPARATUS AND METHOD FOR ACQUIRING ACTIVE NOISE CANCELLATION DATA," each of which is incorporated by reference in its entirety.

II. FIELD

The present disclosure is generally related to acquiring configuration data.

III. DESCRIPTION OF RELATED ART

Advances in technology have resulted in smaller and more powerful computing devices. For example, there currently exist a variety of portable personal computing devices, including wireless computing devices, such as portable wireless telephones, personal digital assistants (PDAs), and paging devices that are small, lightweight, and easily carried by users. More specifically, portable wireless telephones, such as cellular telephones and Internet protocol (IP) telephones, can communicate voice and data packets over wireless networks. Further, many such wireless telephones include other types of devices that are incorporated therein. For example, a wireless telephone can also include a digital still camera, a digital video camera, a digital recorder, and an audio file player. Also, such wireless telephones can process executable instructions, including software applications, such as a web browser application, that can be used to access the Internet. As such, these wireless telephones can include significant computing capabilities.

A wireless telephone may be used with a headset, the wireless telephone enabling two-way communications. Different headset models may have different properties (e.g., acoustic characteristics, pin configurations, programmable control keys, etc.) that may not be readily identifiable to the wireless telephone. Failure to identify these properties may result in degraded headset performance. As a non-limiting example, background noise detected at a particular headset may be disruptive to the communications. To reduce effects of background noise, the wireless telephone or the particular headset may perform active noise cancellation (ANC). For example, the particular headset may capture background noise through microphones and provide a waveform (e.g., a noise signal) of the background noise to a processor of the wireless telephone or the particular headset. In turn, the processor may generate an inverse waveform (e.g., an anti-noise signal) of the background noise and provide the inverse waveform as an output to reduce (or cancel) the background noise.

Performing ANC using a processor of the particular headset may require additional circuitry and may add to the complexity to the particular headset, since headsets that do not perform ANC do not need a processor. Although the wireless telephone may have signal processing capabilities, ANC uses characteristics of the headset to generate the inverse waveform. Thus, the wireless telephone may not have access to information needed to perform ANC. In other scenarios, the wireless telephone may not have access to information to perform other functions (e.g., adjust an input sound gain, adjust an audio output to improve frequency response, perform functions associated with modified pin assignments, perform functions associated with programmable keys, execute applications, etc.) associated with a particular headset.

IV. SUMMARY

This disclosure presents embodiments of an accessory device that includes a memory (e.g., a non-volatile memory, such as an electrical erasable programmable read-only memory (EEPROM)) and an interface (e.g., a single wire low-power bus). When the accessory device is connected to a master device, the master device may retrieve data stored in the memory via the interface and operate the accessory device according to the data. The data may include data associated with speaker parameters of the accessory device, data associated with microphone parameters of the accessory device, data associated with applications that are compatible with the accessory device, data associated with programmable control keys of the accessory device, data associated with audio settings of the accessory device, data associated with pin assignments of the accessory device, active noise cancellation (ANC) coefficients of the accessory device, or any combination thereof.

As a non-limiting example, the master device (e.g., a mobile phone) may be coupled to the accessory device (e.g., a headset) to provide audio output to the accessory device. The accessory device may include ANC circuitry (e.g., one or more ANC microphones and corresponding ANC microphone lines). The accessory device may also include ANC data (e.g., ANC coefficients) that characterizes acoustic properties of the accessory device. A port of the master device may be activated and used to couple the ANC circuitry of the accessory device to a processor within the master device. The accessory device may send identification data to the processor (e.g., via a microphone line). If the processor determines that ANC coefficients (e.g., optimization data to reduce an amount of noise at the headset) for the accessory device are not stored in the master device, the processor may download the ANC coefficients from the non-volatile memory within the accessory device. Alternatively, the processor may download the ANC coefficients from a remote server over a network connection. After acquiring the ANC coefficients, the master device may switch the port from a data communication mode (e.g., two-way communication) to an audio input mode (e.g., one-way communication). The master device may use the ANC coefficients to generate an inverse waveform (e.g., an anti-noise signal) to provide to the accessory device.

In a particular embodiment, an accessory device includes a memory configured to store data and an interface configured to communicate the data from the memory to a master device. The accessory device receives power from the master device.

In another particular embodiment, an accessory device includes a headset with speakers configured to receive audio content from a mobile device. The accessory device also includes a memory configured to store data associated with parameters of the speakers. The accessory device further includes a plug that is compatible to be coupled to a connector of the mobile device. The accessory device also includes an interface configured to communicate the data from the memory to the mobile device via the plug.

In another particular embodiment, an accessory device includes a memory configured to store data associated with an application. The accessory device also includes a plug that is compatible to be coupled to a connector of the mobile device.

The accessory device also includes an interface configured to communicate the data from the memory to the mobile device via the plug.

In another particular embodiment, an accessory device includes a headset and a memory. The headset includes at least one button and speakers that are configured to receive first audio content from a mobile device. The memory is configured to store data associated with at least one function of the at least one button. The accessory device also includes a plug that is compatible to be coupled to a connector of the mobile device. The accessory device further includes an interface configured to communicate the data from the memory to the mobile device via the plug.

In another particular embodiment, an accessory device includes a headset and a memory. The headset includes speakers that are configured to receive audio content from a mobile device. The memory is configured to store data associated with audio settings. The accessory device also includes a plug that is compatible to be coupled to a connector of the mobile device. The accessory device further includes an interface configured to communicate the data from the memory to the mobile device via the plug.

In another particular embodiment, an accessory device includes a plug that is compatible to be coupled to a connector of a mobile device. The connector includes pins configured to electrically connect to a plurality of conducting terminals arranged in series along a length of the plug. The accessory device also includes a memory that is configured to store data associated with functional assignments of the pins in the connector. The accessory device further includes an interface that is configured to communicate the data from the memory to the mobile device via the plug.

In another particular embodiment, an apparatus includes a memory storing instructions executable by a processor to perform operations. The operations include receiving data from a memory of an accessory device. The data includes an identification of the accessory device, a parameter of a part in the accessory device, data associated with an application, data identifying a function of a button on the accessory device, an audio setting, a function of a pin of a connector, or any combination thereof. The operations further include processing the data, generating and/or processing audio content based on the parameter, executing the application, activating the function of the button, generating the audio content according to the audio setting, activating the function of the pin, or any combination thereof.

In another particular embodiment, a method includes receiving data from a memory of an accessory device. The data includes an identification of the accessory device, a parameter of a part in the accessory device, data associated with an application, data identifying a function of a button on the accessory device, an audio setting, a function of a pin of a connector, or any combination thereof. The method also includes processing the data and performing at least one operation. The at least one operation includes generating and/or processing audio content based on the parameter, executing the application, activating the function of the button, generating the audio content according to the audio setting, activating the function of the pin, or any combination thereof.

In another particular embodiment, a computer-readable storage device includes instructions that, when executed by a processor, cause the processor to receive data from a memory of an accessory device. The data includes an identification of the accessory device, a parameter of a part in the accessory device, data associated with an application, data identifying a function of a button on the accessory device, an audio setting, a function of a pin of a connector, or any combination thereof. The instructions are also executable to cause the processor to process the data and perform at least one operation. The at least one operation includes generating and/or processing audio content based on the parameter, executing the application, activating the function of the button, generating the audio content according to the audio setting, activating the function of the pin, or any combination thereof.

In another particular embodiment, an apparatus includes means for receiving data from a memory of an accessory device. The data includes an identification of the accessory device, a parameter of a part in the accessory device, data associated with an application, data identifying a function of a button on the accessory device, an audio setting, a function of a pin of a connector, or any combination thereof. The apparatus also includes means for processing the data and performing at least one operation. The at least one operation includes generating and/or processing audio content based on the parameter, executing the application, activating the function of the button, generating the audio content according to the audio setting, activating the function of the pin, or any combination thereof.

In another particular embodiment, a method includes detecting an accessory device at a master device. The accessory device may receive power from the master device. The method also includes identifying the accessory device based on information received from the accessory device and searching for configuration data associated with the accessory device based on the identification of the accessory device. The method further includes acquiring the configuration data. The configuration data may include data associated with speaker parameters of the accessory device, data associated with microphone parameters of the accessory device, data associated with applications that are compatible with the accessory device, data associated with programmable control keys of the accessory device, data associated with audio settings of the accessory device, active noise cancellation (ANC) coefficients of the accessory device, data associated with pin assignments of the accessory device, or any combination thereof.

In another particular embodiment, an apparatus includes a processor within a master device. The apparatus also includes a memory storing instructions executable by the processor to perform operations. The operations include detecting an accessory device that receives power from the master device and identifying the accessory device based on information received from the accessory device. The operations also include searching for configuration data associated with the accessory device, based on the identification of the accessory device, and acquiring the configuration data. The configuration data may include data associated with speaker parameters of the accessory device, data associated with microphone parameters of the accessory device, data associated with applications that are compatible with the accessory device, data associated with programmable control keys of the accessory device, data associated with audio settings of the accessory device, active noise cancellation (ANC) coefficients of the accessory device, data associated with pin assignments of the accessory device, or any combination thereof.

In another particular embodiment, a computer-readable storage device includes instructions that, when executed by a processor within a master device, cause the processor to detect an accessory device that receives power from the master device and to identify the accessory device based on information received from the accessory device. The computer-readable storage device also includes instructions that, when executed by the processor, cause the processor to search for configuration data associated with the accessory device, based on the identification of the accessory device, and to acquire the configuration data. The configuration data may include data associated with speaker parameters of the accessory device, data associated with microphone parameters of the accessory device, data associated with applications that are compatible with the accessory device, data associated with programmable control keys of the accessory device, data associated with audio settings of the accessory device, active noise cancellation (ANC) coefficients of the accessory device, data associated with pin assignments of the accessory device, or any combination thereof.

In another particular embodiment, an apparatus includes means for acquiring configuration data. Acquiring the configuration data may include detecting an accessory device at a master device. The accessory device receives power from the master device. Acquiring the configuration data may also include identifying the accessory device based on information received from the accessory device and searching for the configuration data associated with the accessory device based on the identification of the accessory device. The apparatus further includes means storing the configuration data. The configuration data may include data associated with speaker parameters of the accessory device, data associated with microphone parameters of the accessory device, data associated with applications that are compatible with the accessory device, data associated with programmable control keys of the accessory device, data associated with audio settings of the accessory device, active noise cancellation (ANC) coefficients of the accessory device, data associated with pin assignments of the accessory device, or any combination thereof.

One particular advantage provided by at least one of the disclosed embodiments is an ability for a mobile phone to acquire (e.g., download) ANC coefficients (or other configuration data) from a particular headset model and/or from a remote source (e.g., a server) to permit the mobile phone to be compatible with a wide range of headset models. As a result, a processor within the mobile phone may generate appropriate waveforms (e.g., anti-noise signals) based on the ANC coefficients to reduce (or cancel) background noise that may otherwise be present at the particular headset model. Other aspects, advantages, and features of the present disclosure will become apparent after review of the entire application, including the following sections: Brief Description of the Drawings, Detailed Description, and the Claims.

V. BRIEF DESCRIPTION OF THE DRAWINGS

VI. DETAILED DESCRIPTION

Figure 1:
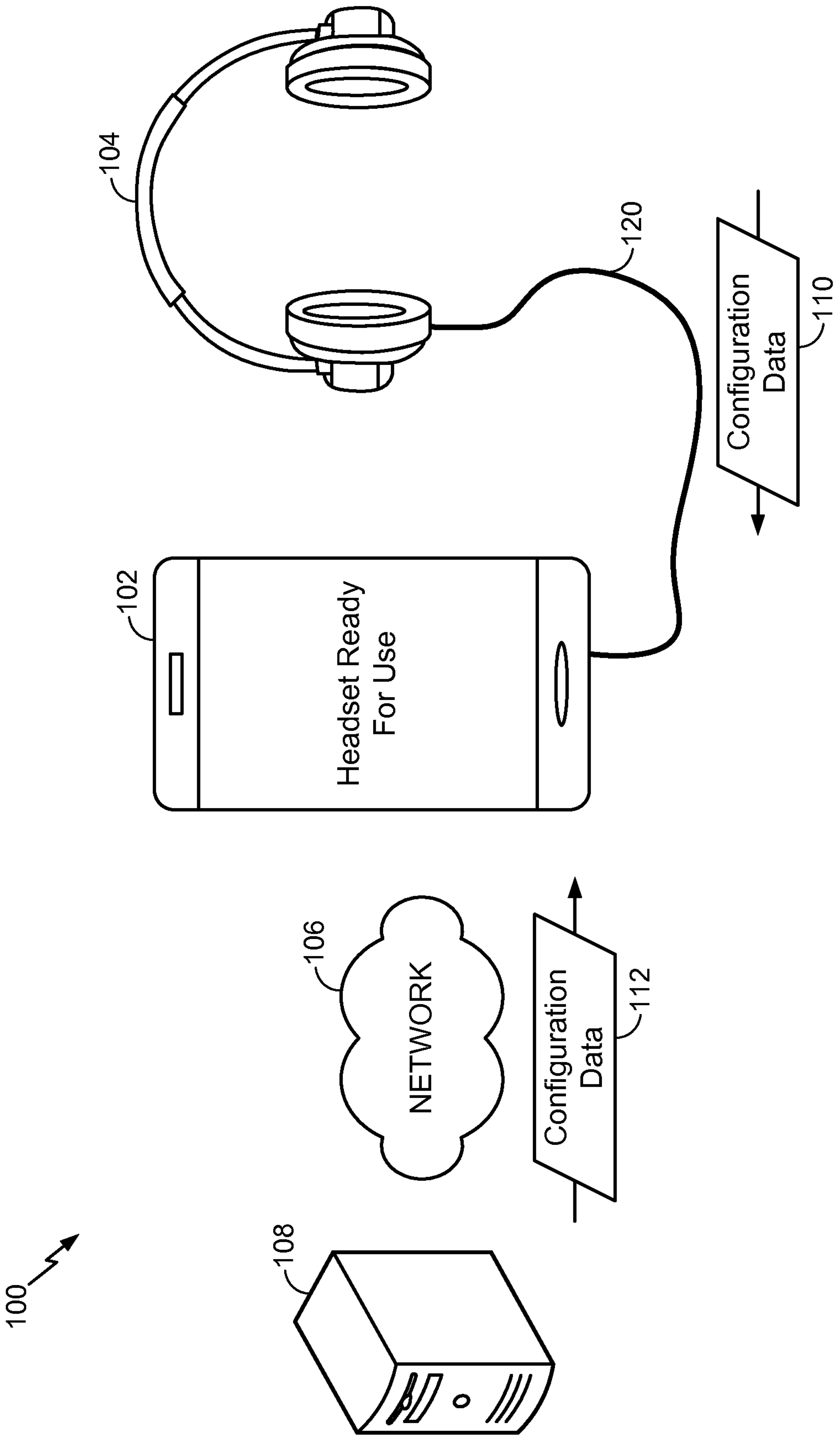
FIG. 1 is a diagram of a particular illustrative embodiment of a system that is operable to facilitate a master device's acquisition of configuration data from an accessory device.

Referring to FIG. 1, a particular illustrative embodiment of a system 100 that is operable to facilitate a master device's acquisition of configuration data from an accessory device is shown. For example, the system 100 may include a master device 102 coupled to an accessory device 104 via a wired connection. In a particular embodiment, the master device 102 may be a mobile phone, and the accessory device 104 may be a headset. The wired connection may include a microphone line 120. The microphone line 120 may be a high impedance communication line between the master device 102 and the accessory device 104. The system 100 may also include a server 108 communicatively coupled to the master device 102 via a network 106.

The master device 102 may be configured to detect the accessory device 104 when the accessory device 104 is coupled to the master device 102. For example, the master device 102 may include a port that is adapted to receive a plug to couple the accessory device 104 to the master device 102. In response to detecting the accessory device 104, the master device 102 may activate a single wire two-way communication mode. In the single wire two-way communication mode, the microphone line 120 may be used to facilitate two-way communication between the master device 102 and the accessory device 104. The master device 102 may transmit a first pulse (e.g., a low pulse or a reset signal) to the accessory device 104 via the microphone line 120 to determine whether the accessory device 104 is compatible with the single wire two-way communication mode. The master device 102 may wait a particular time period for a response (e.g., a second signal or a low pulse) from the accessory device 104. For example, the master device 102 may wait three milliseconds to receive the response from the accessory device 104. If the master device 102 fails to receive the response from the accessory device 104 within the particular time period, the master device 102 may determine that the accessory device 104 is not compatible with the single wire two-way communication mode.

However, if the master device 102 receives the response from the accessory device 104 within the particular time period, the master device 102 may determine that the accessory device 104 is compatible with the single wire two-way communication mode. As a result, data communications may be established between the accessory device 104 and the master device 102 via the microphone line 120.

The master device 102 may also be configured to identify the accessory device 104. For example, the accessory device 104 may transmit identification data to the master device 102 via the microphone line 120. In a particular embodiment, the identification data may include a headset identifier packet (e.g., a 64-bit word). For example, the headset identifier packet may include an 8-bit cyclic redundancy check (CRC) code for security during transmission, a 48-bit serial number that is unique to the model of the accessory device 104 (e.g., the headset model number), and an 8-bit family code corresponding to other applications of the accessory device 104 (e.g., whether the accessory device 104 is an active noise cancellation (ANC) headset, etc.). The master device 102 may receive the identification data from the accessory device 104 via the microphone line 120. The accessory device 104 may be identified by the master device 102 using the identification data. After the master device 102 has identified the accessory device 104, the master device 102 may determine whether configuration data 110, 112 associated with accessory device 104 is stored in a memory of the master device 102.

If the configuration data 110, 112 is stored in the memory of the master device 102, the single wire two-way communication mode may be deactivated and the configuration data 110, 112 may be loaded (e.g., retrieved) from the memory to a processor. However, if the configuration data 110, 112 is not stored in the memory of the master device 102, the master device 102 may search for the configuration data 110, 112 and may attempt to acquire the configuration data 110, 112 from other sources (e.g., the server 108 and/or the accessory device 104).

In a particular embodiment corresponding to a scenario where the accessory device 104 is an ANC headset, the configuration data 110, 112 may include ANC coefficients that characterize acoustic properties of the accessory device 104. The master device 102 may use the ANC coefficients to generate an anti-noise signal (e.g., a signal having an inverse waveform of background noise detected at the accessory device 104) and to provide a modified audio signal (e.g., the anti-noise signal combined with a regular audio signal) to the accessory device 104 to reduce or cancel background noise. An algorithm (e.g., an ANC algorithm) may be used by the master device 102 to determine properties of the anti-noise signal. The ANC coefficients may be used by the algorithm to adjust the properties of the anti-noise signal to be specific to the accessory device 104. For example, the accessory device 104 may include speakers that are configured to receive audio content from the master device 102. The master device 102 may modify the audio content (using the ANC algorithm) based on the ANC coefficients and transmit the modified audio content to the accessory device 104 to reduce an amount of noise at the speakers.

In another particular embodiment, the configuration data 110, 112 may include data associated with speaker parameters. For example, the configuration data 110, 112 may identify a frequency response of the speakers of the accessory device 104, a sound pressure level (SPL) of the speakers, a sealing type of the speakers, a model of the speakers (e.g., Thiele or small), or any combination thereof. The master device 102 may adjust audio provided to the accessory device 104 based on the speaker parameters to improve frequency response at the accessory device 104. In another particular embodiment, the configuration data 110, 112 may include data associated with microphone parameters (e.g., microphone gain offset information). For example, the configuration data 110, 112 may identify the microphone location of the accessory device 104 and/or particular microphone components of the accessory device 104, both which may affect a signal-to-noise ratio (SNR) of sound signals captured by the (microphone of the) accessory device 104. The master device 102 may adjust processing techniques based on the microphone parameters to improve the gain of sound signals received from the accessory device 104.

In another particular embodiment, the configuration data 110, 112 may include data associated with applications that are compatible with the accessory device 104. For example, the configuration data 110, 112 may identify that the accessory device 104 is compatible with sound applications, surround sound, non-audio features, other applications, or any combination thereof. In a particular embodiment, the configuration data 110, 112 may identify that the accessory device 104 is compatible with online payment and/or finance applications (e.g., applications associated with www.paypal.com, www.intuit.com, www.square.com, etc.). The data associated with the applications may enable the master device 102 to run (e.g., perform functions associated with) the applications. In another particular embodiment, the configuration data 110, 112 may include data associated with programmable control keys (e.g., buttons/keys) of the accessory device 104. For example, the configuration data 110, 112 may identify whether the accessory device includes a play button, a pause button, a fast-forward button, a rewind button, buttons used for gaming, voice-call buttons, other buttons, or any combination thereof. The data associated with the particular buttons may enable the master device 102 and/or the accessory device 104 to perform functions associated with the programmable control keys in response to activation of the programmable control keys.

In another particular embodiment, the configuration data 110, 112 may include data associated with audio settings (e.g., bass, treble, equalizer, etc.) of the accessory device 104. In another particular embodiment, the configuration data 110, 112 may include data associated with pin assignments of the accessory device 104. For example, different accessory devices may have different pin assignments that enable functionalities that may not be available with a conventional connector (e.g., a 3.5 mm connector). As non-limiting examples, particular pin assignments may enable high-speed digital communication, higher voltages to charge accessory devices, and/or non-audio functions to be performed. The data associated with the pin assignments may enable the master device 102 to perform functions associated with the modified pin assignments.

In a particular embodiment, the master device 102 may establish a network connection with a remote source and request the configuration data 112 via the network connection. For example, the master device 102 may establish a connection with a server 108 via a network 106. The server 108 may include a database storing the configuration data 112 and identification information (e.g., identifiers of the accessory device 104). For example, a manufacturer of the accessory device 104 may upload the configuration data 112 of the accessory device 104 onto a website that is accessible to the master device 102 via the network 106. Along with the request for the configuration data 112, the master device 102 may send identification information associated with the accessory device 104 to the server 108. The identification information may be based on the identification data received from the accessory device 104. After receiving the request and the identification information, the server 108 may transmit the configuration data 112 (associated with the identification information) to the master device 102 over the network 106. Upon receiving the configuration data 112 from the server 108, the master device 102 may load the configuration data 112 to the processor to perform functions (e.g., generate an anti-noise signal, modify pin arrangements, improve gain of received sound signals, etc.).

In another particular embodiment, the master device 102 may request the configuration data 110 from the accessory device 104 via the microphone line 120. As explained with respect to FIG. 2, the accessory device 104 may include a memory (e.g., an electrically erasable programmable read-only memory (EEPROM)) that stores the configuration data 110. For example, the manufacturer of the accessory device 104 may store the configuration data 110 in the memory of the accessory device 104 during or after manufacturing. The memory (and the accessory device 104) may receive power from the master device 102 via the microphone line 120. In response to receiving the request for the configuration data 110, the accessory device 104 may transmit the configuration data 110 to the master device 102 via the microphone line 120. Upon receiving the configuration data 110 from the memory of the accessory device 104, the master device 102 may load the configuration data 110 to the processor to perform functions.

After the master device 102 receives the configuration data 110, 112 from the accessory device 104 and/or the server 108, the single wire two-way communication mode may be deactivated. For example, digital ports within the master device 102 may be set to a high impedance level, and the microphone line 120 may be released (e.g., decoupled from the memory of the accessory device 104) and used to transmit audio signals in only one direction (e.g., to the master device 102). For example, a main microphone (shown in FIG. 3) of the accessory device 104 may be used to transmit audio (e.g., speech and/or background noise) to the master device 102.

Acquiring the configuration data 110, 112 from the accessory device 104 and/or the server 108 may permit the master device 102 to be compatible with a wide range of accessory devices (e.g., a wide range of headset models) by adjusting processor functionality at the master device 102 based on configuration data specific to a particular accessory device. As a non-limiting example, each accessory device may store appropriate ANC coefficients in a memory of the accessory device and transfer the ANC coefficients to the master device 102 when the accessory device is connected to the master device 102 for the first time. The ANC coefficients may be stored in a memory of the master device 102 after the ANC coefficients are transferred to the master device 102. As a result, the ANC coefficients may be used (e.g., retrieved from the memory) the next time that the particular accessory device is connected to the master device 102. Thus, acquiring the configuration data 110 from the accessory device 104 may increase the likelihood that the configuration data 110 matches the headset model and decrease the likelihood that improper data is used by the master device 102. Further, seamlessly transferring the configuration data 110, 112 from the accessory device 104 or the server 108, respectively, may eliminate a manual setup process by a user of the master device 102.

Figure 2:
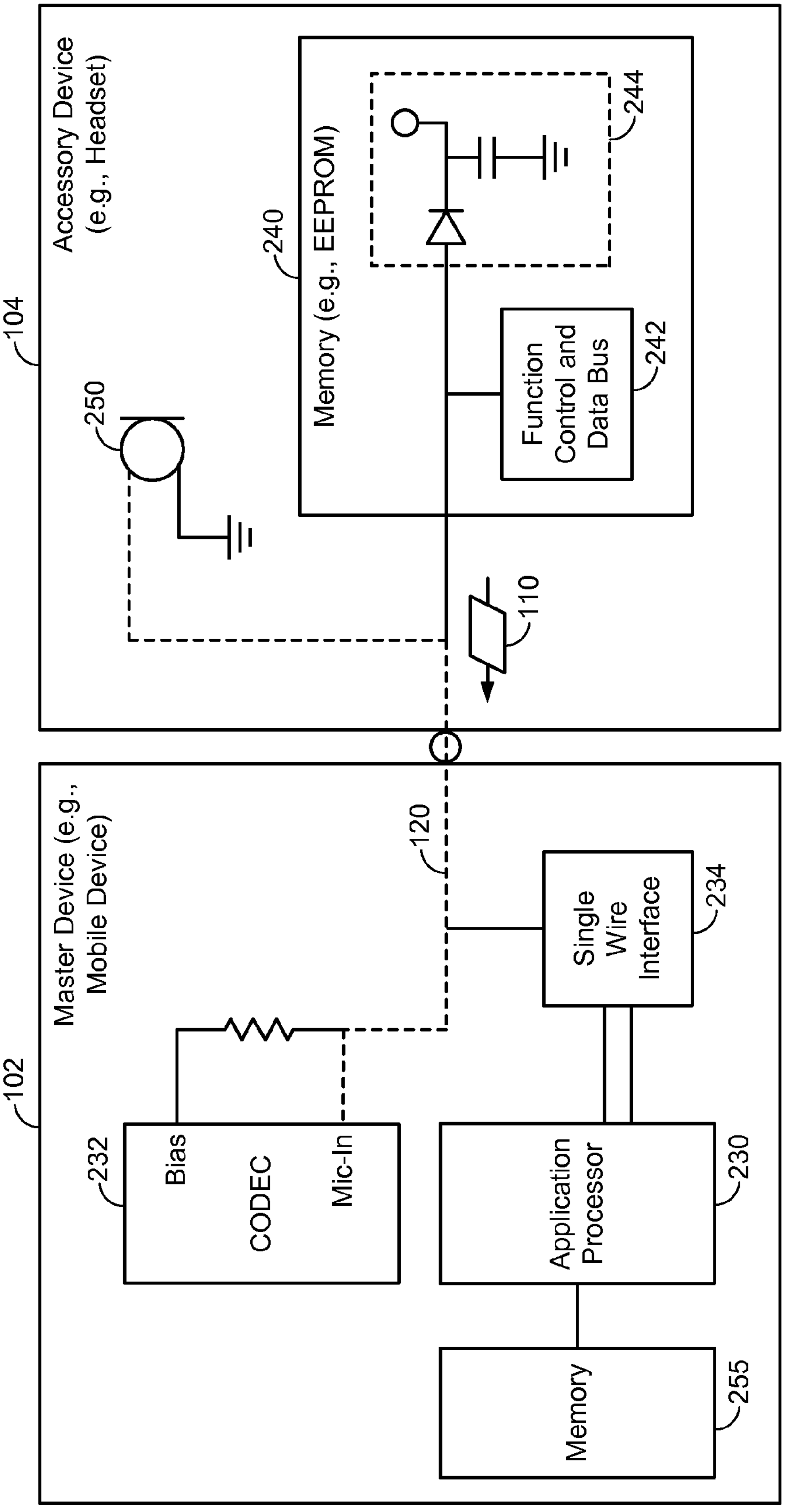
FIG. 2 is a diagram of a particular embodiment of a master device and an accessory device of the system of FIG. 1.

Referring to FIG. 2, a particular illustrative embodiment of the master device 102 and the accessory device 104 of FIG. 1 is shown. The master device 102 may include an application processor 230, an audio encoder/decoder (CODEC) 232, and a single wire interface 234. In a particular embodiment, the single wire interface 234 may be included in the application processor 230. The accessory device 104 may include a memory 240. In a particular embodiment, the accessory device 104 may include a main microphone 250. In another particular embodiment, the accessory device 104 may include two speakers and two ANC microphones (as described with respect to FIG. 3) without a main microphone.

The application processor 230 may be configured to detect the accessory device 104 when the accessory device 104 is coupled to the master device 102. For example, a signal may be transmitted to the application processor 230 indicating that a device (e.g., the accessory device 104) has been connected to a port of the master device 102. The application processor 230 may be configured to detect capabilities of a device when the device is plugged into the master device 102. As a non-limiting example, when a plug of the device is coupled to the port of the master device 102, the configuration of the plug may be used by the master device 102 to detect whether the device corresponds to a headset without a microphone, a headset that includes a standard microphone, or an ANC headset that includes a standard microphone and ANC microphones.

The application processor 230 may activate the single wire two-way communication mode using the single wire interface 234 and may transmit the first pulse (e.g., a low pulse or a reset signal) to the accessory device 104 via the microphone line 120 to determine whether the accessory device 104 is compatible with the single wire two-way communication mode. The application processor 230 may wait a particular time period for a response from the accessory device 104.

If the application processor 230 fails to receive a response from the accessory device 104 within a particular time period, the application processor 230 may determine that the accessory device 104 is not compatible with the single wire two-way communication mode. If the application processor 230 receives the response from the accessory device 104 within the particular time period, the application processor 230 may determine that the accessory device 104 is compatible with the single wire two-way communication mode. As a result, data communications may be established between the application processor 230 and a function control and data bus 242 via the microphone line 120.

In a particular embodiment, the memory 240 of the accessory device 104 may be an electrically erasable programmable read-only memory (EEPROM). The memory 240 may include, or be coupled to, the function control and data bus 242 and a parasitic power unit 244. The parasitic power unit 244 may include a diode and a capacitor that are configured to power the memory 240 in response to receiving a voltage signal from a communication bus (e.g., the microphone line 120). In a particular embodiment, the memory 240 derives all of its operational power from the master device (e.g., via the microphone line 120). The function control and data bus 242 may be configured to provide a response (e.g., a low pulse) to the application processor 230 via the microphone line 120 in response to receiving the transmit pulse.

The function control and data bus 242 may transmit identification data to the master device 102 via the microphone line 120. The application processor 230 may receive the identification data from the function control and data bus 242 at the single wire interface 234. The accessory device 104 may be identified by the master device 102 using the identification data.

After the application processor 230 has identified the accessory device 104, the application processor 230 may determine whether configuration data for the accessory device 104 (e.g., corresponding to the identification data) is stored in a memory 255 of the master device 102. When configuration data for the accessory device 104 is not stored in the memory 255 of the master device 102, the application processor 230 may request that the configuration data 110 be sent from the memory 240 of the accessory device 104 via the microphone line 120. In response to receiving the request for the configuration data 110, the function control and data bus 242 may transmit the configuration data 110 to the application processor 230 via the microphone line 120.

After receiving the configuration data 110 from the accessory device 104 or accessing the configuration data from the memory 255, the application processor 230 may deactivate single wire two-way communication mode by setting the single wire interface 234 to a high impedance level and releasing the microphone line 120 (e.g., decoupling the microphone line 120 from the memory 240 and the application processor 230). Deactivating the single wire two-way communication mode enables the microphone line 120 to transmit audio signals to the master device 102. For example, audio detected at the main microphone 250 may be transmitted to the audio CODEC 232 via the microphone line 120.

The application processor 230, or another processor (not shown) of the master device 102, may use the configuration data 110 to perform processing functions. For example, in the scenario where the configuration data 110 corresponds to ANC coefficients, the master device 102 may use the configuration data 110 to generate an anti-noise signal. The anti-noise signal may be combined with an audio signal to generate a modified audio signal, and the modified audio signal may be provided to the audio CODEC 232 to reduce or cancel background noise at the accessory device 104. For example, the audio CODEC 232 may be configured to output the modified audio signal (e.g., a sound signal to be projected through a speaker of the accessory device 104). The modified audio signal may be transmitted to the accessory device 104 via a left speaker line (shown in FIG. 3), a right speaker line (shown in FIG. 3), or any combination thereof. Thus, the application processor 230, or another processor, may generate the anti-noise signal based on the ANC coefficients using the ANC algorithm; and the application processor 230, or another processor, may combine the anti-noise signal with the audio signal to generate a modified audio signal that reduces noise detected at the accessory device 104. Thus, the master device 102 may modify the audio signal based on the ANC coefficients and transmit the modified audio signal to speakers (not shown) in the accessory device 104.

In the scenario where the configuration data 110 corresponds to speaker parameters, the master device 102 may use the configuration data 110 to adjust audio provided to the accessory device 104 based on the speaker parameters to improve frequency response at the accessory device. In the scenario where the configuration data 110 corresponds to microphone parameters (e.g., microphone gain offset information), the master device 102 may use processing techniques to improve the gain of sound signals received from the accessory device 104.

Acquiring the configuration data 110 from the memory 240 may permit the master device 102 to be compatible with a wide range of accessory devices 104 (e.g., a wide range of headset models) by adjusting processor functionality based on configuration data 110 specific to a particular accessory device 104. Thus, acquiring the configuration data 110 from the accessory device 104 may increase the likelihood that the configuration data 110 matches the headset model of the accessory device 104 and may decrease the likelihood that improper data (e.g., configuration data not associated with the accessory device 104) is used by the master device 102.

Figure 3:
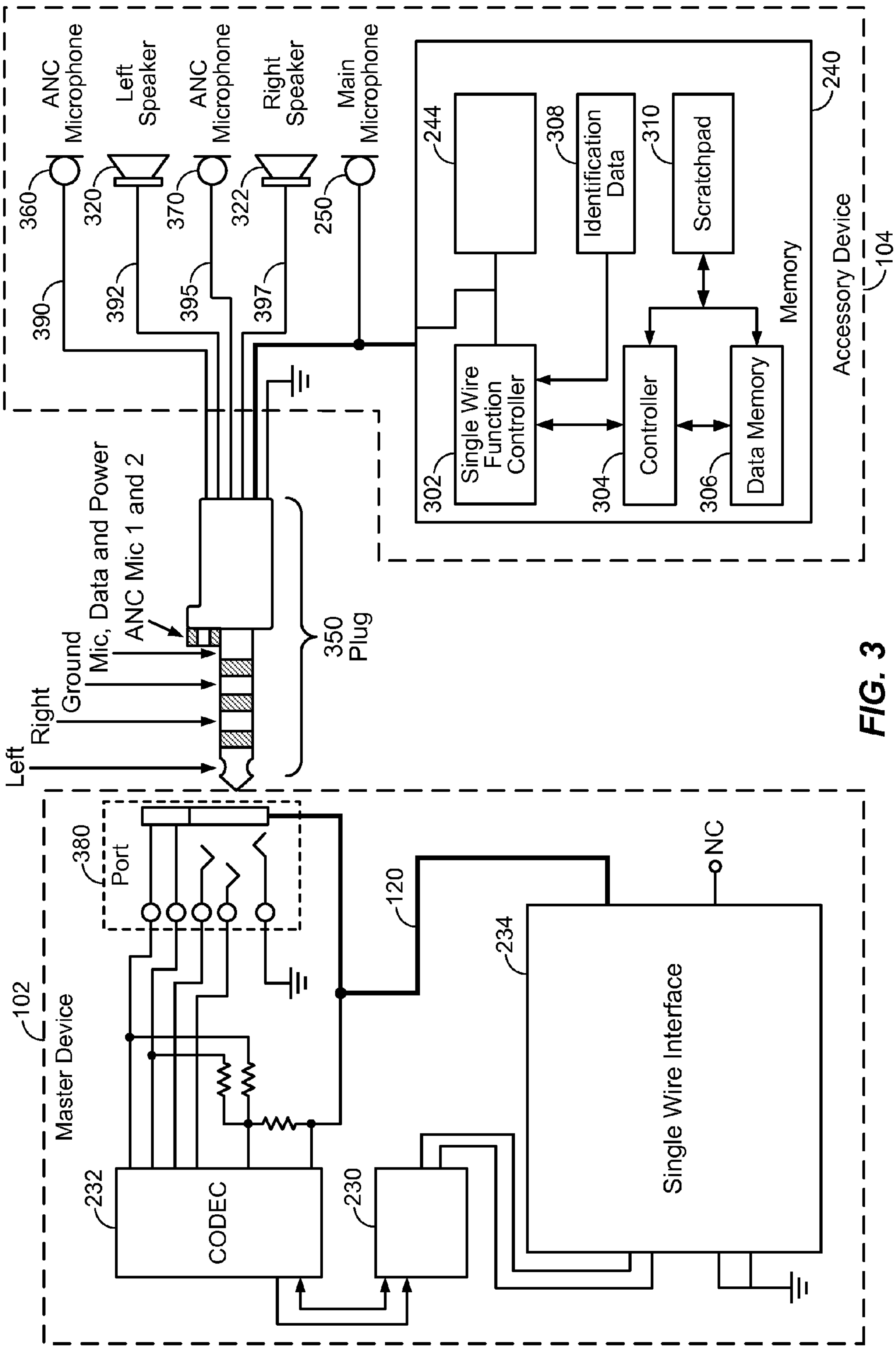
FIG. 3 is a diagram of another particular embodiment of a master device and an accessory device of the system of FIG. 1.

Referring to FIG. 3, a particular illustrative embodiment of the master device 102 and the accessory device 104 of FIG. 1 is shown. The master device 102 may include the application processor 230, the audio CODEC 232, a port 380, and the single wire interface 234. The accessory device 104 may include the main microphone 250, the memory 240, a plug 350, a left speaker 320 (e.g., a left earpiece), a right speaker 322 (e.g., a right earpiece), a left ANC microphone 360, and a right ANC microphone 370. The single wire interface 234 may be configured to switch the port 380 between operation in a single wire two-way communication mode and a single wire one-way communication mode. In the single wire two-way communication mode, the single wire interface 234 may use an Inter-Integrated Circuit ($I^2C$) protocol to communicate data from the master device 102 to the accessory device 104 and from the accessory device 104 to the master device 102. In the single wire one-way communication mode, the single wire interface 234 may communicate audio from the accessory device 104 to the master device 102.

The plug 350 may be configured to be inserted into the port 380 of the master device 102. The master device 102 may detect the accessory device 104 in response to the plug 350 being inserted into the port 380. The plug 350 may include pins that come into contact with corresponding pins of the port 380 which are coupled to the audio CODEC 232. For example, the plug 380 may include a “left” pin that couples the left speaker 320 to a left output of the audio CODEC 232 that is configured to output audio intended to be projected by the left speaker 320. The plug 380 may include a “right” pin that couples the right speaker 322 to a right output of the audio CODEC 232 that is configured to output audio intended to be projected by the right speaker 322. The plug 380 may include a “microphone” pin configured to couple the main microphone 250 to an input of the audio CODEC 232 via the microphone line 120. The microphone line 120 may also be used for two-way communication between the master device 102 and the accessory device 104. For example, the configuration data 110 (e.g., ANC coefficients) may be transferred from the memory 240 to the application processor 230 using the “microphone” pin and the microphone line 120.

The plug 380 may also include a “left ANC microphone” pin that couples the left ANC microphone 360 to an input of the audio CODEC 232. The left ANC microphone 360 may be configured to detect audio (e.g., background noise) near the left speaker 320 and to provide the detected audio to the master device 102 via a first ANC microphone line 390. The plug 380 may also include a “right ANC microphone” pin that couples the right ANC microphone 370 to an input of the audio CODEC 232. The right ANC microphone 370 may be configured to detect audio (e.g., background noise) near the right speaker 322 and to provide the detected audio to the master device 102 via a second ANC microphone line 395. Background noise detected at the ANC microphones 360, 370 may be provided to the audio CODEC 232 and used to generate the anti-noise signal. For example, the background noise detected at the ANC microphones 360, 370 may correspond to a noise signal. The application processor 230, or another processor, may generate an inverse waveform of the noise signal (e.g., the anti-noise signal) and provide the inverse waveform to the speakers 320, 322 via speaker lines 392, 397, respectively, to reduce (or cancel) the noise detected by the ANC microphones 360, 370.

The memory 240 may include the parasitic power unit 244, a single wire function controller 302, a memory controller 304, a data memory 306, identification data 308, and a scratchpad 310. As described with respect to FIG. 2, the microphone line 120 may be coupled to the parasitic power unit 244 to provide power to the memory 240. For example, voltage signals may be transferred from the master device 102 to the parasitic power unit 244 via the microphone line 120.

The single wire function controller 302 may be configured to receive data from the master device 102 via the microphone line 120 and to covert the data into a format (e.g., a language) that is compatible with the memory 240. The single wire function controller 302 may also be configured to adjust a voltage level of a signal received from the master device 102, to send signals to the master device 102 from the memory 240, to control timing of the signals communicated with the master device 102, and to release (e.g., decouple) the microphone line 120 from the memory 240 after configuration (e.g., after the master device 102 receives the configuration data 110 from the memory 240).

The identification data 308 may include a headset registration number (e.g., a 64-bit word). For example, the identification data 308 may include an 8-bit CRC code, a 48-bit serial number that is unique to the model of the accessory device 104 (e.g., the headset model number), and an 8-bit family code. The identification data 308 may be transmitted to the master device 102 upon request via the single wire function controller 302 and the microphone line 120.

The memory controller 304 may be configured to initiate the transmission of data (e.g., the identification data 308, the configuration data 110, and/or other data stored in the memory 240) to the master device 102. For example, the configuration data 110 may be stored in particular locations of the data memory 306. In a particular embodiment, the data memory 306 may include 80 32-byte pages. The memory controller 304 may fetch the configuration data 110 from the particular location in the data memory 306 and initialize the transfer of the configuration data 110 from the memory 240 to the master device 102. The memory controller 304 may utilize the scratchpad 310 to write to the data memory 306. In a particular embodiment, the scratchpad 310 may include a 32-byte scratchpad used by the memory controller 304 to write data into each page of the data memory 306.

During an ANC operation, the master device 102 and the accessory device 104 may be used to make voice calls, listen to music, and/or other applications. For example, audio signals (e.g., audio signals from voice calls, music files, etc.) may be projected through the speakers 320, 322 of the accessory device 104. During a voice call, the main microphone 250 may receive a voice input and the ANC microphones 360, 370 may receive noise (e.g., ambient noise and/or background noise) along with some of the voice input. A noise signal corresponding to the noise may be provided to the plug 350 via the ANC microphone lines 390, 395 and may be transmitted to the application processor 230 (or another processor) via the port 380 and the audio CODEC 232. The application processor 230 (or another processor) may generate the anti-noise signal (e.g., a signal having an inverse waveform of the noise signal) and may mix the anti-noise signal with output audio to generate a modified audio signal. The modified audio signal may be provided to the speakers 320, 322 via the speaker lines 392, 397 to reduce (or cancel) the effect of noise at the accessory device 104.

Figure 4:
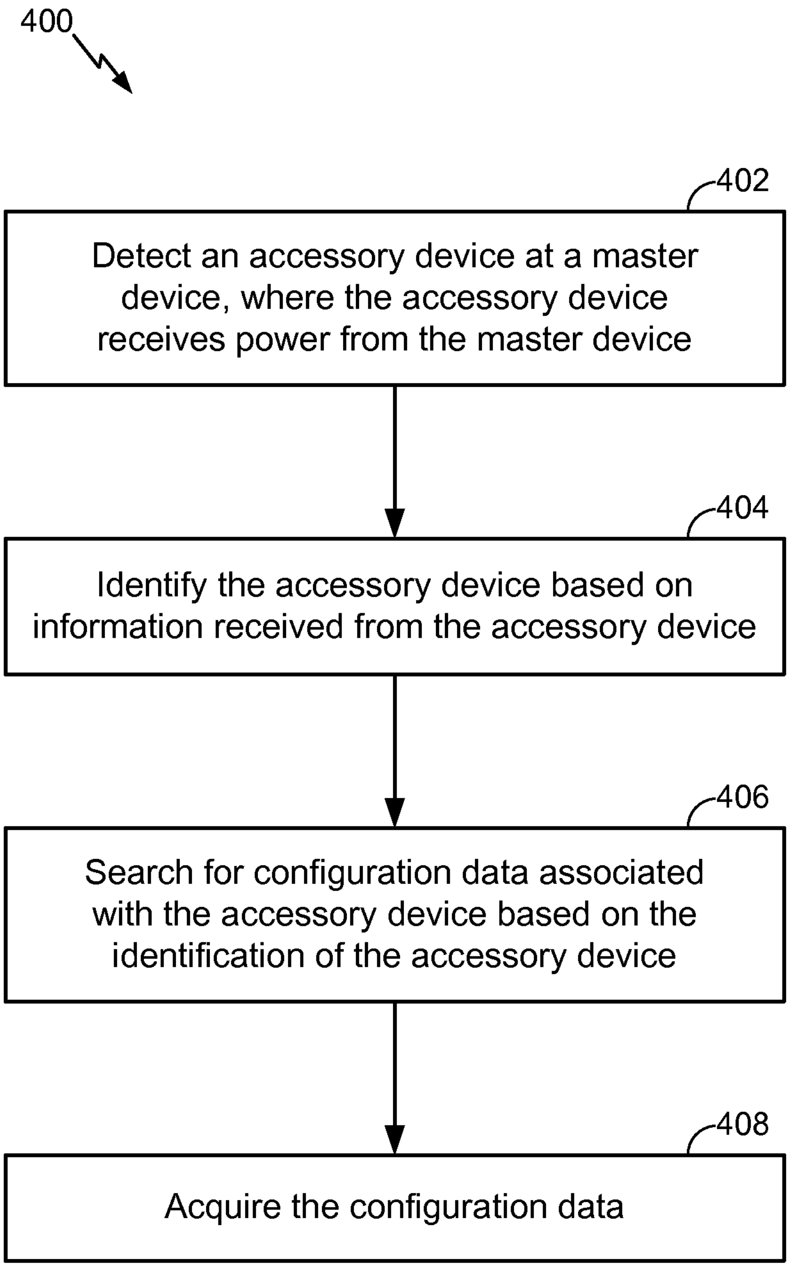
FIG. 4 is a flowchart of a particular embodiment of a method of acquiring configuration data.

Referring to FIG. 4, a flowchart of a particular embodiment of a method 400 of acquiring configuration data is shown. In an illustrative embodiment, the method 400 may be performed using the system 100 of FIG. 1, the master device 102 of FIGS. 1-3, or any combination thereof.

The method 400 includes detecting an accessory device at a master device, at 402. For example, in FIG. 1, the master device 102 may include a port that is adapted to receive a plug of the accessory device 104. The master device 102 may detect the accessory device 104 when the plug of the accessory device 104 is connected to the port of the master device 102. As another example, the application processor 230 of FIG. 2 may detect the accessory device 104 when the accessory device 104 is connected to the master device 102. For example, a signal may be transmitted to the application processor 230 indicating that a device (e.g., the accessory device 104) has been connected to the port of the master device 102.

The accessory device may be identified based on information received from the accessory device, at 404. For example, in FIG. 1, the accessory device 104 may transmit identification data to the master device 102 via the microphone line 120 in response to receiving the first signal (e.g., the reset signal) from the master device 102. The identification data may include a headset identifier packet (e.g., a 64-bit word). The master device 102 may receive the identification data from the accessory device 104 at the single wire interface 234. The accessory device 104 may be identified by the master device 102 using the identification data.

Configuration data associated with the accessory device may be searched for based on the identification of the accessory device, at 406. For example, in FIG. 1, the master device 102 may determine whether configuration data 110, 112 associated with the accessory device 104 are stored in the memory of the master device 102. If the configuration data 110, 112 is not stored within the memory of the master device 102, the master device 102 may establish a network connection with a remote source and request the configuration data 112 via the network connection. For example, the master device 102 may establish a connection with the server 108 via the network 106. The server 108 may include a database storing the configuration data 112. Alternatively, the application processor 230 of FIG. 2 may request that the configuration data 110 be sent from the accessory device 104 via the microphone line 120.

The configuration data may be acquired, at 408. For example, in FIG. 1, the server 108 may transmit the configuration data 112 to the master device 102 over the network 106 in response to receiving the request. Alternatively, the accessory device 104 may transmit the configuration data 110 to the master device 102 via the microphone line 120 in response to receiving the request for the configuration data 110. After receiving the configuration data 110, the master device 102 may perform functions (e.g., generate anti-noise signals, adjust an audio output to improve frequency response, perform functions associated with modified pin assignments, perform functions associated with programmable keys of the accessory device 104, run applications, etc.) based on the configuration data 110. The master device 102 may also store the configuration data 110 in the memory of the master device 102 for future use when the accessory device 104 is coupled to the master device 102.

The method 400 of FIG. 4 may permit that master device 102 to acquire the configuration data 110, 112 from the accessory device 104 or the server 108, respectively, in response to a determination that acoustic characteristics and/or other properties of the accessory device 104 are unknown to the master device 102 (e.g., the configuration data 110, 112 is not stored in the memory of the master device 102). As a result, the method 400 may permit the master device 102 to be compatible with a wide range of accessory devices 104 (e.g., a wide range of headset models) by adjusting processor functions of the master device 102 based on configuration data 110, 112 specific to a particular accessory device 104.

Figure 5:
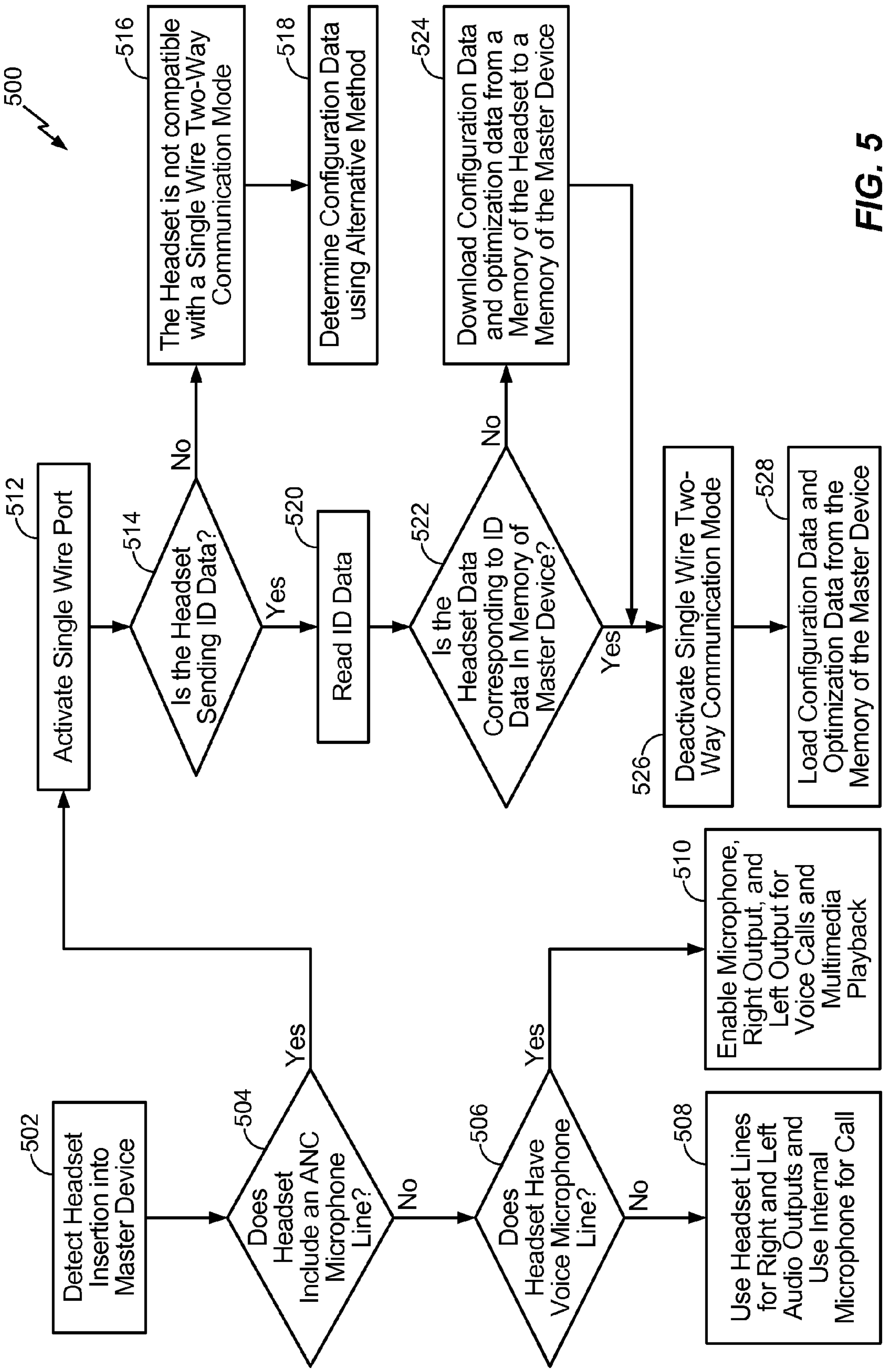
FIG. 5 is a flowchart of a particular embodiment of a method of acquiring active noise cancellation data.

Referring to FIG. 5, a flowchart of a particular embodiment of a method 500 of acquiring active noise cancellation data is shown. In an illustrative embodiment, the method 500 may be performed using the system 100 of FIG. 1, the master device 102 of FIGS. 1-3, or any combination thereof.

At 502, a master device 102 may detect an insertion of a headset (e.g., the accessory device 104). For example, in FIG. 1 or FIG. 2, the master device 102 may detect when a plug of the accessory device 104 is connected to a port of the master device 102.

At 504, the master device 102 may determine whether the headset includes ANC microphone lines 390, 395. If the headset includes ANC microphone lines 390, 395, the method 500 moves to 512. If the headset does not include ANC microphone lines 390, 395, the method 500 moves to 506. At 506, the master device 102 determines whether the headset includes a microphone line 120. If the headset includes a microphone line 120, the master device 102 may enable the microphone line 120, left speaker 320, and the right speaker 322 for voice calls and multimedia playback, at 510. If the headset does not include a microphone line 120, the master device 102 may use the headset lines for audio outputs and an internal microphone for voice calls, at 508.

At 512, when the headset includes ANC microphone lines 390, 395, the master device 102 may activate a single wire port. For example, in FIG. 2, the application processor 230 may activate the single wire interface 234 to enable single wire two-way communication. The master device 102 may determine whether the headset is sending identification data, at 514. For example, in FIG. 1, the master device 102 may transmit the first pulse to the headset via the microphone line 120 to determine whether the headset is compatible with a single wire two-way communication mode. If the headset is not compatible with the single wire two-way communication mode, the method 500 moves to 516 and configuration data may be determined using alternative methods (e.g., manual user input and/or download), at 518. If the headset is compatible with the single wire two-way communication mode, the master device 102 may read identification data of the headset, at 520. For example, the headset may transmit the identification data to the master device 102 via the microphone line 120. The identification data may be a 48-bit serial number included in a headset identifier packet (e.g., a 64-bit word). The master device 102 may receive the identification number from the headset at the single wire interface 234. The headset may be identified by the master device 102 using the identification number.

At 522, the master device 102 may determine whether headset data corresponding to the identification data is in a memory of the master device 102 (e.g., whether the configuration data 110, 112 is within the memory of the master device 102). If the headset data is within the memory of the master device 102, the master device 102 may deactivate the single wire two-way communication mode, at 426, and load the configuration data 110 from the memory, at 528. If the headset data is not at the memory of the master device 102, the master device 102 may download the configuration data 110 from the memory 240 of the headset (e.g., the EEPROM), at 524.

The method 500 of FIG. 5 may permit that master device 102 to acquire configuration data (e.g., ANC coefficients) from the headset in response to a determination that acoustic characteristics and/or other properties of the headset are unknown to the master device 102 (e.g., the configuration data 110 is not stored in the memory of the master device 102). As a result, the method 500 may permit the master device 102 to be compatible with a wide range of headset models. Although steps 512-528 are illustrated as being dependent on the headset having an ANC microphone line, at 504, in other embodiments, steps 512-528 may be independent of a determination of whether the headset has an ANC microphone line. For example, the single wire port may be activated, at 512, in response to detecting that the headset has been inserted into the master device, at 502. Thus, the steps 512-528 may be utilized for configuration data that is not limited to ANC coefficients.

Figure 6:
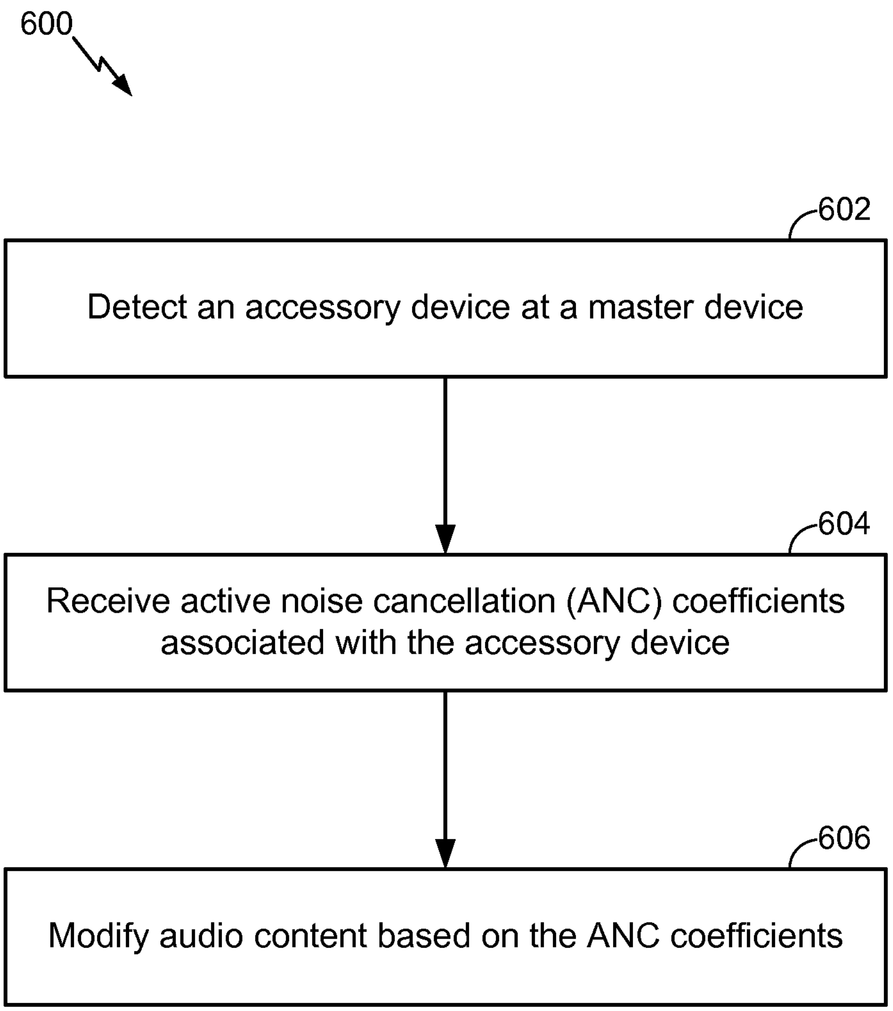
FIG. 6 is a flowchart of another particular embodiment of a method of acquiring active noise cancellation data.

Referring to FIG. 6, a flowchart of another particular embodiment of a method 600 of acquiring active noise cancellation data is shown. In an illustrative embodiment, the method 600 may be performed using the system 100 of FIG. 1, the master device 102 of FIGS. 1-3, or any combination thereof.

The method 600 includes detecting an accessory device at a master device, at 602. For example, referring to FIG. 1, the master device 102 may include a port that is adapted to receive a plug of the accessory device 104. The master device 102 may detect the accessory device 104 when the plug of the accessory device 104 is connected to the port of the master device 102. As another example, the application processor 230 of FIG. 2 may detect the accessory device 104 when the accessory device 104 is connected to the master device 102. For example, a signal may be transmitted to the application processor 230 indicating that a device (e.g., the accessory device 104) has been connected to the port of the master device 102.

Active noise cancellation (ANC) coefficients associated with the accessory device may be received, at 604. For example, in FIG. 1, the server 108 may transmit the configuration data 112 to the master device 102 over the network 106 in response to receiving a request. Alternatively, the accessory device 104 may transmit the configuration data 110 to the master device 102 via the microphone line 120 in response to receiving a request for the configuration data 110. The configuration data 110, 112 may correspond to ANC coefficients. The master device 102 may search for the ANC coefficients (e.g., send the request for ANC coefficients to the server 108 and/or to the accessory device 104) based on an identification of the accessory device 104.

Audio content may be modified based on the ANC coefficients, at 606. For example, in FIG. 1, after receiving the configuration data 110, 112 (e.g., the ANC coefficients), the master device 102 may use the ANC coefficients to generate an anti-noise signal (e.g., a signal having an inverse waveform of background noise detected at the accessory device 104) and to provide a modified audio signal (e.g., the anti-noise signal combined with a regular audio signal) to the accessory device 104 to reduce or cancel background noise. An algorithm (e.g., an ANC algorithm) may be used by the master device 102 to determine properties of the anti-noise signal. The ANC coefficients may be used by the algorithm to adjust the properties of the anti-noise signal to be specific to the accessory device 104. For example, the accessory device 104 may include speakers that are configured to receive audio content from the master device 102. The master device 102 may modify the audio content (using the ANC algorithm) based on the ANC coefficients and transmit the modified audio content to the accessory device 104 to reduce an amount of noise at the speakers.

The method 600 of FIG. 6 may permit the master device 102 to acquire configuration data (e.g., ANC coefficients) from the headset in response to a determination that acoustic characteristics and/or other properties of the headset are unknown to the master device 102 (e.g., the configuration data 110 is not stored in the memory of the master device 102). As a result, the method 600 may permit the master device 102 to be compatible with a wide range of headset models.

Figure 7:
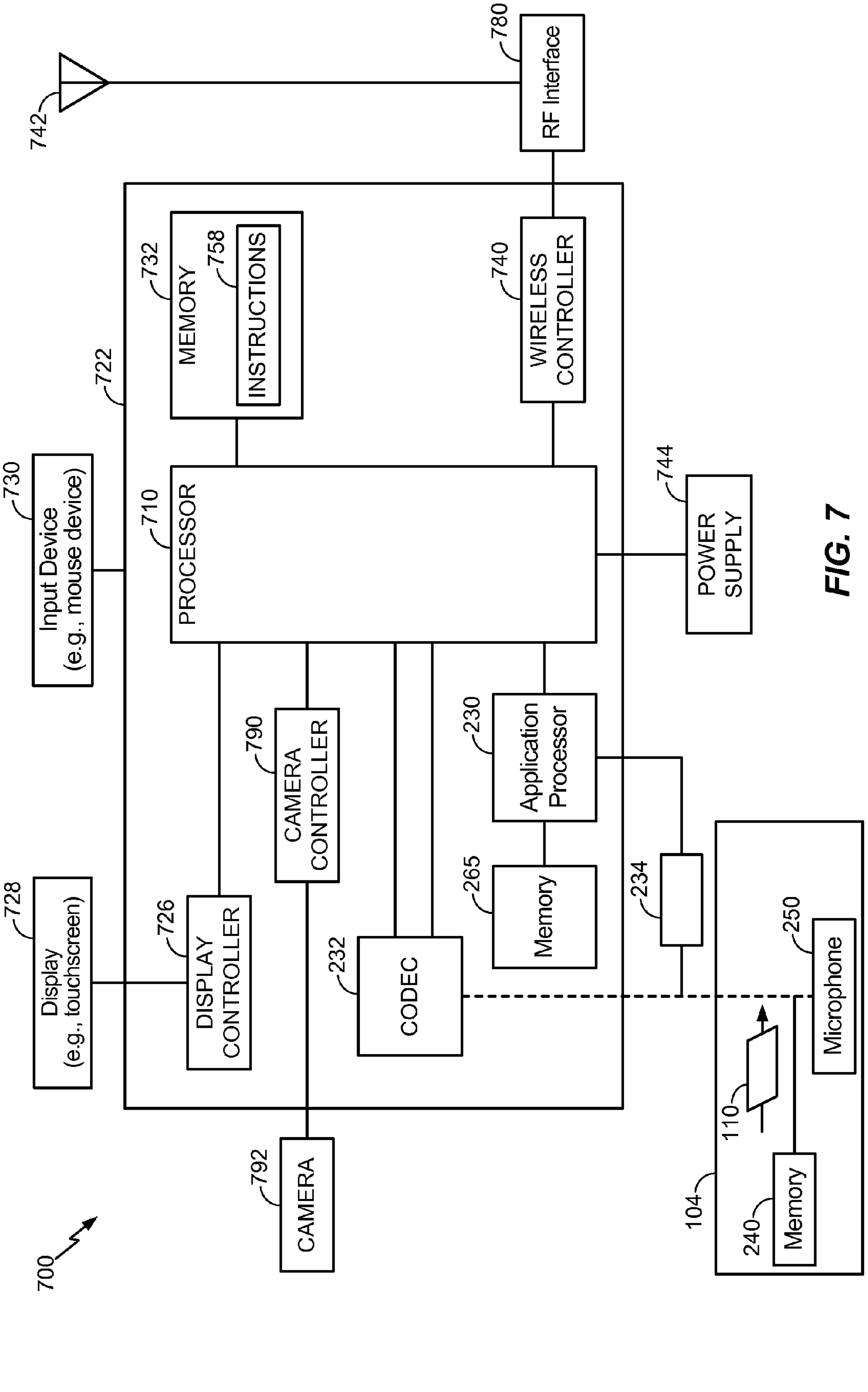
FIG. 7 is a block diagram of a wireless device including components that are operable to configuration data.

Referring to FIG. 7, a block diagram of a wireless device 700 including components that are operable to acquire configuration data is shown. The wireless device 700 includes a main processor 710, such as a digital signal processor (DSP), coupled to a main memory 732.

FIG. 7 also shows a display controller 726 that is coupled to the main processor 710 and to a display 728. A camera controller 790 may be coupled to the main processor 710 and to a camera 792. In a particular embodiment, the wireless device 700 may correspond to the master device 102. For example, the wireless device 700 includes the audio CODEC 232, the single wire interface 234, and the application processor 230. The audio CODEC 232 may be coupled to the main processor 710 and the application processor 230 may be coupled to the main processor 710. The single wire interface 234 may be coupled to the application processor 230.

The accessory device 104 may be coupled to the wireless device 700. For example, the accessory device 104 may be coupled to the CODEC 232 and to the single wire interface 234 via the microphone line 120. The accessory device 104 includes the memory 240 that is configured to transmit the configuration data 110 to the application processor 230 via the microphone line 120. The application processor 230 may relay the configuration data 110 to the main processor 710.

In a particular embodiment where the configuration data 110 corresponds to ANC coefficients, after the main processor 710 receives the configuration data 110, ANC microphones (not shown in FIG. 7), such as the ANC microphones 360, 370 of FIG. 3, may be used to detect background noise (and some user speech in some instances). The background noise detected at the ANC microphones may be provided to main processor 710 as a noise signal via ANC microphone lines (not shown in FIG. 7), such as the ANC microphone lines 390, 395 in FIG. 3. The main processor may generate an anti-noise signal by inputting the ANC coefficients into the ANC algorithm. The main processor 710 may combine the anti-noise signal with an audio signal (e.g., user speech, MP3 audio, etc.) to generate a modified audio signal. The single wire interface 234 may be set to high impedance and the microphone line 120 may be decoupled from the application processor 230 and the memory 240. The modified audio signal may be provided to the accessory device 104 via the audio CODEC 232. In a particular embodiment, the modified audio signal may be provided to the accessory device 104 via a left speaker line (not shown) coupled to a left speaker (not shown) of the accessory device 104, a right speaker line (not shown) coupled to a right speaker (not shown) of the accessory device 104, or any combination thereof. The main microphone 250 may be used to detect audio (e.g., user speech) and transmit the detected audio to the main processor 710 via the audio CODEC 232 and the microphone line 120.

The main memory 732 may be a tangible non-transitory processor-readable storage medium that includes instructions 758. The instructions 758 may be executed by a processor, such as the main processor 710, the application processor 230, or the components thereof, to perform the method 400 of FIG. 4, the method 500 of FIG. 5, the method 600 of FIG. 6, or any combination thereof FIG. 7 also indicates that a wireless controller 740 can be coupled to the main processor 710 and to the antenna 742 via a radio frequency (RF) interface 780. In a particular embodiment, the main processor 710, the display controller 726, the main memory 732, the CODEC 232, the camera controller 790, the application processor 230, the single wire interface 234, and the wireless controller 740 are included in a system-in-package or system-on-chip device 722. In a particular embodiment, as illustrated in FIG. 7, the display 728, an input device 730, the antenna 742, the accessory device 104, the RF interface 780, a power supply 744, and the single wire interface 234 are external to the system-on-chip device 722. However, each of the display 728, the input device 730, the microphone 718, the antenna 742, the accessory device 104, the RF interface 780, the power supply 744, and the single wire interface 234 can be coupled to a component of the system-on-chip device 722, such as an interface or a controller.

In conjunction with the described embodiments, a first apparatus is disclosed that includes means for acquiring configuration data. For example, the means for acquiring may include the master device 102 of FIGS. 1-3, the single wire interface 234 of FIG. 2, the microphone line 120 of FIGS. 1-2, the port 380 of FIG. 3, the application processor 230 programmed to execute the instructions 758 of FIG. 7, the main processor 710 programmed to execute the instructions 758 of FIG. 7, one or more other devices, circuits, or modules to acquire the configuration data, or any combination thereof.

The first apparatus may also include means for storing the configuration data. For example, the means for storing the ANC coefficients may include the master device 102 of FIGS. 1-3, memory 255 of FIG. 2, one or more other devices, circuits, or modules to store the configuration data, or any combination thereof.

In conjunction with the described embodiments, a second apparatus is disclosed that includes means for acquiring ANC coefficients. For example, the means for acquiring the ANC coefficients may include the master device 102 of FIGS. 1-3, the single wire interface 234 of FIG. 2, the microphone line 120 of FIGS. 1-2, the port 380 of FIG. 3, the application processor 230 programmed to execute the instructions 758 of FIG. 7, the main processor 710 programmed to execute the instructions 758 of FIG. 7, one or more other devices, circuits, or modules to acquire the ANC coefficients, or any combination thereof.

The second apparatus may also include means for modifying audio content based on the ANC coefficients. For example, the means for modifying audio content may include the master device 102 of FIGS. 1-3, the application processor 230 programmed to execute the instructions 758 of FIG. 7, the main processor 710 programmed to execute the instructions 758 of FIG. 7, one or more other devices, circuits, or modules to acquire the ANC coefficients, or any combination thereof.

Those of skill would further appreciate that the various illustrative logical blocks, configurations, modules, circuits, and algorithm steps described in connection with the embodiments disclosed herein may be implemented as electronic hardware, computer software executed by a processor, or combinations of both. Various illustrative components, blocks, configurations, modules, circuits, and steps have been described above generally in terms of their functionality. Whether such functionality is implemented as hardware or processor executable instructions depends upon the particular application and design constraints imposed on the overall system. Skilled artisans may implement the described functionality in varying ways for each particular application, but such implementation decisions should not be interpreted as causing a departure from the scope of the present disclosure.

The steps of a method or algorithm described in connection with the embodiments disclosed herein may be embodied directly in hardware, in a software module executed by a processor, or in a combination of the two. A software module may reside in random access memory (RAM), flash memory, read-only memory (ROM), programmable read-only memory (PROM), erasable programmable read-only memory (EPROM), electrically erasable programmable read-only memory (EEPROM), registers, hard disk, a removable disk, a compact disc read-only memory (CD-ROM), or any other form of non-transient storage medium known in the art. An exemplary storage medium is coupled to the processor such that the processor can read information from, and write information to, the storage medium. In the alternative, the storage medium may be integral to the processor. The processor and the storage medium may reside in an application-specific integrated circuit (ASIC). The ASIC may reside in a computing device or a user terminal. In the alternative, the processor and the storage medium may reside as discrete components in a computing device or user terminal.

The previous description of the disclosed embodiments is provided to enable a person skilled in the art to make or use the disclosed embodiments. Various modifications to these embodiments will be readily apparent to those skilled in the art, and the principles defined herein may be applied to other embodiments without departing from the scope of the disclosure. Thus, the present disclosure is not intended to be limited to the embodiments shown herein but is to be accorded the widest scope possible consistent with the principles and novel features as defined by the following claims.

What is claimed is:

1. A method comprising:

detecting an accessory device by a master device;

based on determining that the accessory device includes an active noise cancellation (ANC) microphone line, requesting, by the master device, ANC coefficients associated with the accessory device; and modifying audio content, at the master device, based on the ANC coefficients.

2. The method of claim 1, wherein the accessory device corresponds to a headset comprising speakers configured to receive the modified audio content from the master device.

3. The method of claim 2, further comprising transmitting the modified audio content to the headset to reduce an amount of noise at the speakers.

4. The method of claim 2, wherein the headset further comprises a memory configured to store data associated with acoustic characteristics of the speakers.

5. The method of claim 4, wherein the data includes the ANC coefficients.

6. The method of claim 1, further comprising identifying the accessory device based on information received from the accessory device, wherein the ANC coefficients are received based on identifying the accessory device.

7. The method of claim 6, wherein identifying the accessory device comprises:

determining whether the accessory device is compatible with a single wire two-way communication mode in response to a determination that the accessory device includes the ANC microphone line; and receiving identification data from the accessory device based on a determination that the accessory device is compatible with the single wire two-way communication mode, wherein the master device identifies the accessory device based on the identification data.

8. The method of claim 6, further comprising:

establishing a network connection; and receiving the ANC coefficients from a remote source via the network connection.

9. The method of claim 8, wherein the ANC coefficients are requested from the remote source via the network connection.

10. The method of claim 1, further comprising receiving the ANC coefficients from the accessory device at the master device, wherein the ANC coefficients are received from a memory within the accessory device via a microphone line of the accessory device, the microphone line distinct from the ANC microphone line.

11. The method of claim 1, further comprising determining whether the accessory device is compatible with a single wire two-way communication mode in response to a determination that the accessory device includes the ANC microphone line.

12. The method of claim 1, further comprising receiving identification data from the accessory device based on a determination that the accessory device is compatible with a single wire two-way communication mode, wherein the master device identifies the accessory device based on the identification data.

13. The method of claim 1, further comprising receiving, at the master device, the ANC coefficients from a remote source via a network connection.

14. The method of claim 1, wherein the ANC coefficients are requested from a remote source via a network connection.

15. The method of claim 1, wherein modifying the audio content includes:

receiving, at the master device, a background noise signal from the accessory device via the ANC microphone line;

generating, by the master device, an anti-noise signal based on the background noise signal and the ANC coefficients, wherein the anti-noise signal includes an inverse signal of the background noise signal; and combining, by the master device, the anti-noise signal with an audio signal of the audio content.

16. The method of claim 1, further comprising:

determining a connection between at a first connector of the master device and a second connector of the accessory device prior to detecting the accessory device; and determining that the accessory device includes the ANC microphone line based on detecting a configuration of the second connector.

17. An apparatus comprising:

a processor within a master device; and a memory storing instructions executable by the processor to perform operations comprising:

detecting an accessory device at the master device;

requesting active noise cancellation (ANC) coefficients associated with the accessory device based on determining that the accessory device includes an ANC microphone line; and modifying audio content based on the ANC coefficients.

18. The apparatus of claim 17, wherein the accessory device corresponds to a headset comprising speakers configured to receive the modified audio content from the master device.

19. The apparatus of claim 18, wherein the headset further comprises an electrical erasable programmable read only memory (EEPROM) configured to store data associated with acoustic characteristics of the speakers, and wherein the data includes the ANC coefficients.

20. The apparatus of claim 17, wherein the operations further comprise identifying the accessory device based on information received from the accessory device, wherein the ANC coefficients are received based on identifying the accessory device.

21. The apparatus of claim 20, wherein identifying the accessory device comprises receiving identification data from the accessory device based on a determination that the accessory device is compatible with a single wire two-way communication mode, wherein the master device identifies the accessory device based on the identification data.

22. The apparatus of claim 20, wherein the ANC coefficients are requested from a remote source via a network connection.

23. The apparatus of claim 22, further comprising an antenna configured to receive the ANC coefficients from the remote source via the network connection.

24. The apparatus of claim 17, further comprising a first connector configured to receive a second connector of the accessory device, wherein the first connector includes a first pin associated with the ANC microphone line and a second pin associated with a second ANC microphone line, the ANC microphone line distinct from the second ANC microphone line.

25. A computer-readable storage device comprising instructions that, when executed by a processor within a master device, cause the processor to:

detect an accessory device;

request active noise cancellation (ANC) coefficients associated with the accessory device based on determining that the accessory device includes an ANC microphone line; and modify audio content based on the ANC coefficients.

26. The computer-readable storage device of claim 25, further comprising instructions that, when executed by the processor, cause the processor to request that the ANC coefficients be sent from the accessory device to the master device, wherein the ANC coefficients are received from an electrical erasable programmable read only memory (EEPROM) within the accessory device, and wherein the EEPROM is powered by the master device.

27. The computer-readable storage device of claim 25, further comprising instructions that, when executed by the processor, cause the processor to:

identify the accessory device based on information received from the accessory device; and establish a network connection, wherein the ANC coefficients are requested from a remote source via the network connection and requested based on identifying the accessory device, wherein the ANC coefficients are received from the remote source via the network connection, and wherein the ANC coefficients are received based on identifying the accessory device.

28. An apparatus comprising:

means for detecting an accessory device at a master device;

means for requesting active noise cancellation (ANC) coefficients associated with the accessory device based on determining that the accessory device includes an ANC microphone line; and means for modifying audio content, at the master device, based on the ANC coefficients.

29. The apparatus of claim 28, further comprising means for providing power to a non-volatile memory of the accessory device, and wherein the accessory device corresponds to a headset comprising speakers configured to receive the modified audio content from the master device.

30. The apparatus of claim 28, further comprising means for receiving the ANC coefficients from a remote source via a network connection or from a memory within the accessory device based on an identification of the accessory device.

* * * * *